US006638216B1

(12) United States Patent  (10) Patent No.: US 6,638,216 B1
Durell  (45) Date of Patent: Oct. 28, 2003

(54) VARIABLE VIEW ARTHROSCOPE (75) Inventor: William E. Durell, N. Barrington, IL (US)

(73) Assignee: Durell & Gitelis, Inc., North Barrington, IL (US)

( * ) Notice: Subject to any disclaimer, the term of this patent is extended or adjusted under 35 U.S.C. 154(b) by 214 days.

(21) Appl. No.: 09/650,621

(22) Filed: Aug. 30, 2000

(51) Int. Cl.[7] .................................................. A61B 1/00
(52) U.S. Cl. ........................ 600/173; 600/129; 600/171
(58) Field of Search ................................ 600/173, 176, 600/130, 131, 106, 107; 385/119; 433/30

(56) References Cited

U.S. PATENT DOCUMENTS

| | | | |
|---|---|---|---|
| 1,726,268 A | * | 8/1929 | Jahr .............................. 600/173 |
| 2,932,294 A | | 4/1960 | Fourestier et al. |
| 2,987,960 A | | 6/1961 | Sheldon |
| 3,357,433 A | | 12/1967 | Fourestier et al. |
| 3,643,654 A | | 2/1972 | Felbarg |
| 3,856,000 A | | 12/1974 | Chikama |
| 3,880,148 A | * | 4/1975 | Kanehira et al. ............ 600/173 |
| 3,901,220 A | | 8/1975 | Koyasu et al. |
| 3,918,438 A | | 11/1975 | Hayamizu et al. |
| 4,140,364 A | | 2/1979 | Yamashita et al. |
| 4,191,468 A | * | 3/1980 | Scully ............................ 356/17 |
| 4,640,577 A | | 2/1987 | Tsuno |
| 4,697,577 A | | 10/1987 | Forkner |
| 4,723,843 A | | 2/1988 | Zobel |
| 4,838,247 A | | 6/1989 | Forkner |
| 4,846,154 A | | 7/1989 | MacAnnally et al. |
| 4,858,002 A | | 8/1989 | Zobel |
| 4,877,314 A | | 10/1989 | Kanamori |
| 5,184,602 A | | 2/1993 | Anapliotis et al. |
| 5,424,877 A | | 6/1995 | Tsuyuki et al. |
| 5,603,687 A | | 2/1997 | Hori et al. |
| 5,613,936 A | | 3/1997 | Czarnek et al. |
| 5,643,176 A | * | 7/1997 | Persidsky ..................... 600/173 |
| 5,743,846 A | | 4/1998 | Takahashi et al. |
| 6,110,105 A | | 8/2000 | Durell |
| 6,139,490 A | | 10/2000 | Briedenthal et al. |
| 6,364,830 B1 | | 4/2002 | Durell |
| 6,371,909 B1 | * | 4/2002 | Hoeg et al. ................... 600/173 |

FOREIGN PATENT DOCUMENTS

| WO | WO 95/25460 | 9/1995 |
|---|---|---|
| WO | WO 99/42028 | 8/1999 |

* cited by examiner

Primary Examiner—John P. Leubecker
(74) Attorney, Agent, or Firm—Hale & Dorr, LLP (57) ABSTRACT A variable-view arthroscope or similar instrument (endoscope, etc.) includes a housing tube with an object input end. The housing tube contains an object input assembly and a portion of a light relay assembly. The object input assembly includes an input lens and a first mirror. In some embodiments, the object input assembly includes a second mirror, and in alternative embodiments, the object input assembly includes a prism. The object input assembly passes images received from a viewing area to an object relay assembly that transmits the image object to the control end of the arthroscope. In some embodiments, the light relay assembly is formed of two mirrored rods. A control varies the position of the object input assembly to change the a viewing position of the arthroscope. In some embodiments, the control includes a push rod driven by a slide and cam/axle assembly.

24 Claims, 11 Drawing Sheets

VARIABLE VIEW ARTHROSCOPE

Field of the Invention

The invention relates generally to arthroscopes, endoscopes and similar optical instruments and more specifically to variable view arthroscopes.

BACKGROUND OF THE INVENTION

Arthroscopes and similar optical instruments, such as endoscopes, are used in medical applications, such as suirgery and examination, as well as in non-medical applications that similarly involve visual inspection of a confined or inaccessible space that constitutes the working area. Although the present invention is described here with reference to an arthroscope or similar instrument employed for surgery, the invention may be useful for other applications and is intended to embrace all suitable variations.

Over the last fifteen or more years, minimally invasive surgery has become a mainstream surgical technique. Within the orthopedic field, in particular, arthroscopy and similar techniques that employ devices such as arthroscopes have become the most common surgical procedures. Minimally invasive surgery is less painful for the patient and, in most instances, can be performed more quickly and safely than surgery that requires greater invasion of the patient's body; other benefits of minimally invasive surgery include that administration of anesthesia is simpler for minimally invasive surgery, that patients heal more quickly, that hospital stays may be reduced in length or even eliminated, and that the procedures are more cost effective.

The value of using minimally invasive surgical techniques may be limited by the capabilities of the arthroscopes, endoscopes and other principal optical instruments employed. In particular, the rather limited field of view afforded by even the best available instruments that satisfy the dimensional and other requirement of surgical applications has limited the useful scope of minimally invasive surgical techniques. Typically, the larger the field of view, the greater the usefulness of the instrument for most applications.

Several methods for widening the field of view offered by arthroscopic/endoscopic instruments have been proposed, but they have not been especially successful. Generally, such proposals have required packing a plurality of movable lenses or prisms into the input end of the instrument; the resulting problems of precision of construction, precision of relative movements, space requirements, optical distortions, and elimination of undesired ambient light have been substantial.

Illuminating the viewing area to obtain a usable image is another requirement of arthroscopes and similar instruments. Without adequate light, the resultant image does not contain sufficient information to be maximally useful. Light is typically provided to the object input end of the arthroscope from an external source through a light guide. The light from the external source is transferred to an internal light guide in the arthroscope at one end of the arthroscope and transmitted to the distal end of the arthroscope via the internal light guide, where the light generally diffuses to light the viewing area around the distal end of the arthroscope. The external source typically includes a light connected to a fiber optic bundle; the external fiber optic bundle is mechanically coupled to the internal light guide, which is typically also a fiber optic bundle. Typically, the external source and the internal optical fiber light guide are standard parts that are commercially available. The coupling efficiency, that is, the amount of light that actually passes from the light source to the viewing area, is relatively poor.

The poor coupling efficiency results in part from the difficulty in controlling the light emitted from the external source fiber optic bundle and focusing that light into the internal light guide and in part from the physical structure of a bundle of optical fibers. Matching the numerical aperture and spot size of the external source in the receiving internal light guide is very important for coupling efficiency. The numerical aperture of an optical fiber is a mathematical representation (the sine of the half angle of the full cone of light that can be accepted by the optical fiber and completely transmitted without any loss) of the angle at which light may strike the surface of an optical fiber that is perpendicular to the optical axis of the fiber and still travel down the fiber. Light that strikes that surface at too great an angle as measured from the optical axis of the fiber, i.e. exceeds the numerical aperture of the fiber, will be lost. The spot size of a light beam is defined by the circular area within which a large percentage of the light is contained at a particular distance from the source of the light beam. The most efficient light transfer occurs when the transmitted light falls within the numerical aperture of the receiving fibers and the spot size of the transmitted light is smaller than the core of the receiving fiber. A focusing lens or focusing system may be used to aid in directing the light from the source appropriately. Typically, if the spot size of the external light source is reduced by a focusing lens, then the cone angle of the converging light from the focusing lens may exceed the numerical aperture of the receiving fiber, and the light that exceeds the numerical aperture of the receiving fiber will be lost. Conversely, if the cone angle of the converging light is less than the numerical aperture of the receiving fiber, then the spot size of the converging light may be larger than the core size of the receiving fiber, and the light that exceeds the core size of the receiving fiber will be lost. Matching the numerical aperture and spot size of the source fiber to those of a receiving fiber, such as between the external light source and the internal light guide, can be especially difficult when the source is a bundle of fibers. Also, when attempting to focus light from a bundle of fibers into a second bundle of fibers, the coupling efficiency is greatly reduced because a single focusing system is attempting to focus a group of spots simultaneously. Since only one ray is actually on the focusing system optical centerline, all other rays from the source fibers, as they spread out from the center of each fiber, are decentered and unsymmetrical in the focusing lens. They therefore cannot match both the spot size and numerical aperture of the receiving fibers. The greatest coupling efficiency is achieved through a compromise between the spot size and the cone angle of the converging light, i.e., when the converging light most nearly matches the core size and numerical aperture of the receiving fiber and when the optical centerlines of the emitting fiber, the focusing system, and the receiving fiber are coaxial.

An additional problem that leads to poor light transmission to the viewing area results from the construction of bundles of fibers. A single optical fiber consists of a core (the light carrying portion) and the cladding (the covering of the core that causes the light to stay contained within the core). Only the cores of the bundled fibers carry light; therefore, light is lost due to the spaces between the cores. When a group of fibers having circular cross-sections is bundled into a cylindrical configuration, only about 78% of the cross-sectional area of the cylindrical configuration is taken up by fibers. Also, the core of each of the bundled fibers is smaller than the cladding. Consequently, the actual light-carrying area is significantly smaller than the circular cross-section of the bundle. Improved light transmission to the distal end of the arthroscope will improve the illumination of the viewing area and increase the information contained in captured images.

There is a need for an arthroscope that affords a wide effective field of view and that does not require movement of the arthroscope to vary its scope of view. One such arthroscope is disclosed in copending U.S. application Ser. No. 09/243,845, entitled "Variable View Arthroscope;" which has a common inventor with the present application. Another such arthroscope is disclosed in copending U.S. application Ser. No. 09/452,340, entitled "Variable View Arthroscope;" which also has a common inventor with the present application. The referenced applications are incorporated herein by this reference. There is also a need for an improved light relay system for illuminating the viewing area through an arthroscope. In this specification and in the appended claims the term "arthroscopd" means and should be interpreted to include an endoscope or any other similar optical instrument, whether used for surgery or otherwise.

SUMMARY OF THE INVENTION

A variable view arthroscope in accordance with the present invention includes a variable object input assembly in an elongated housing tube, a control to vary the view of the object input assembly, and a lighting assembly to illuminate the viewing area. An input window, located in the input end of the housing tube, allows a view of the working area. The input window is preferably spherical. The object input assembly includes an input lens, a first mirror, and a second mirror. The input lens is movable and the first mirror is rotatable. The input lens and the first mirror move around the same axle. The second mirror is fixed. The reflected light from the viewing area forms a working image and the light image or object rays pass from the viewing area through the input window and the input lens, reflect from the first mirror to the second mirror, and reflect from the second mirror into a relay lens system. In some embodiments, the second mirror may be replaced by a prism.

The control varies the position of the input lens and first mirror to any position, or to a series of fixed positions, between a first limit position and a second limit position. As object rays pass through the input lens to the first mirror, to the second mirror or prism, and into the relay lens system, the length of the axial ray remains the same when the angle of view of the arthroscope changes. Also, the lengths of the rim rays may be equal to each other and may also remain the same when the angle of view of the arthroscope changes.

In another aspect of the invention, the lighting assembly preferably includes a relay light guide formed from one or more rods of transparent material with mirrored surfaces. The relay light guide preferably captures each light ray from an external source and transmits the ray to the viewing area.

BRIEF DESCRIPTION OF THE DRAWINGS

For a fuller understanding of the present invention, reference should be made to the following detailed description taken in connection with the accompanying drawings, not drawn to scale, in which the same reference numerals indicate the same or similar parts, wherein.

DESCRIPTION OF THE PREFERRED EMBODIMENTS

Figure 1:
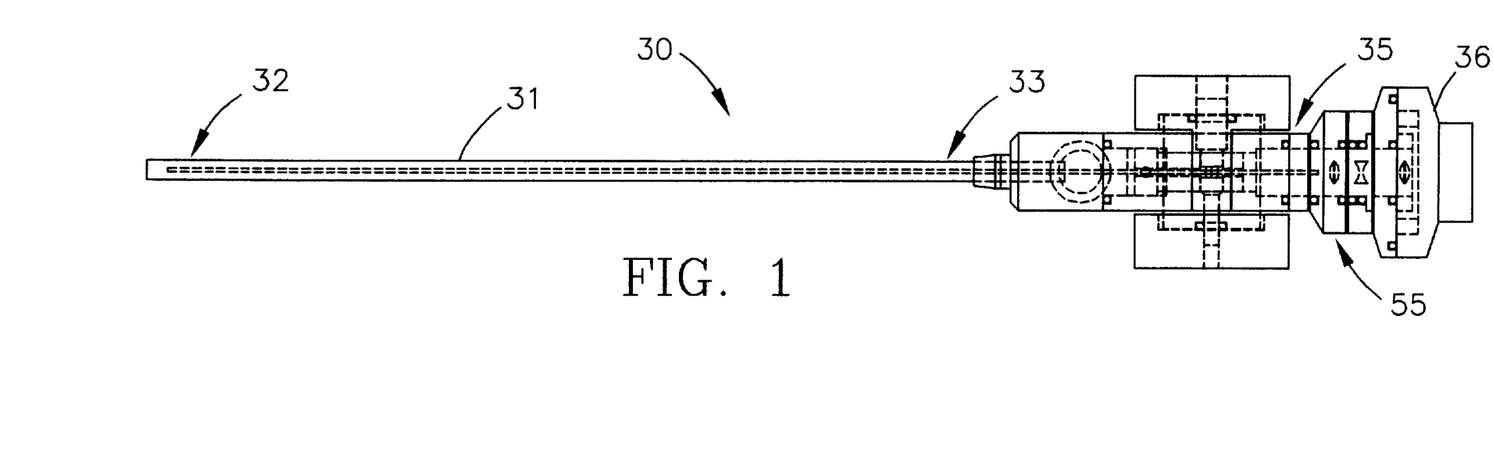
FIG. 1 is a plan view of a variable view arthroscope in accordance with an embodiment of the present invention.
Figure 2:
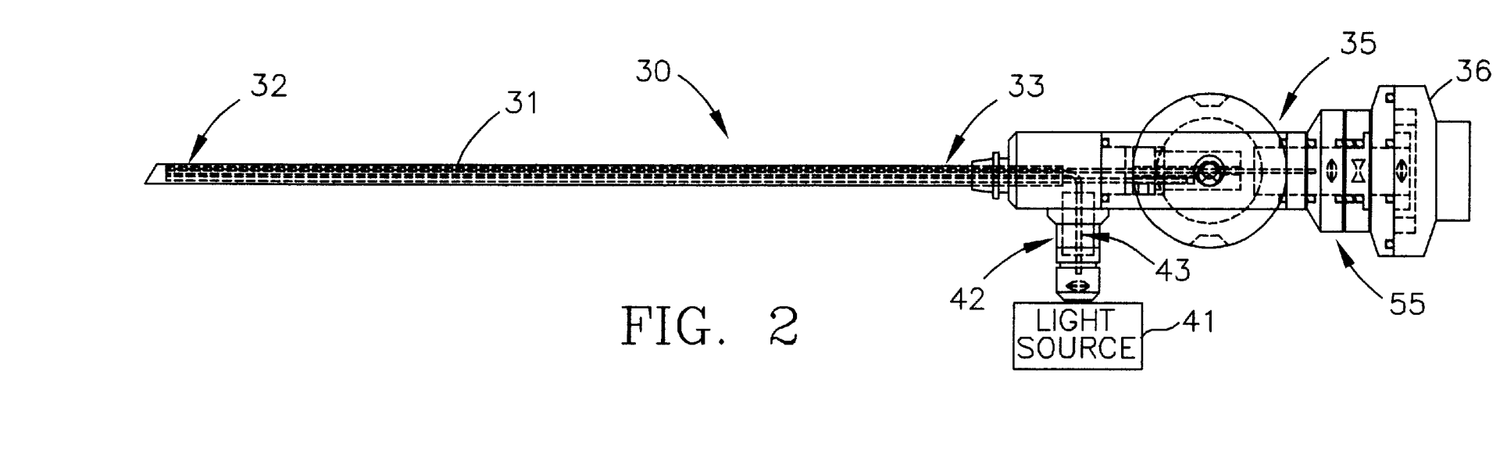
FIG. 2 is a sectional elevation view of the variable view arthroscope of FIG. 1.

A variable view arthroscope in accordance with an embodiment of the present invention is shown in FIGS. 1 and 2. Although shown and described herein as an arthroscope providing up-down view variability, a similar configuration could be oriented so as to provide side-to-side view variability or view variability along any other axis. A variable view arthroscope, generally indicated at 30, includes an elongated housing tube 31, with an object input end 32 and a control end 33, that extends along a central, longitudinal axis. Arthroscope 30 includes an outer control portion 35. Housing tube 31, and more specifically its control end 33, may extend into the outer control portion 35 of arthroscope 30. Generally, an image object is captured at the object input end 32 of housing tube 31, relayed to the control end 33, and recorded and displayed from the outer control portion 35 of arthroscope 30. As discussed herein, the image object is formed of object rays and the object rays include an axial ray at the optical center of the object image, and rim rays at the outer edges or rims of the object image.

The control portion 35 ends with a CCD attachment 36. The CCD attachment 36 is connected by appropriate means to an image screen (not shown) to be viewed by a person using arthroscope 30. CCD attachment 36 may be of conventional construction and is not shown in detail. The outer control portion 35 may also include a control, such as a slide, for adjusting the view of the arthroscope 30, and a focusing lens assembly 55 for adjusting the focus of the arthroscope 30. The focusing lens assembly 55 may include a focusing lens, a zoom lens, and their controls. The focusing lens assembly directs the object received from the input end 32 into the CCD attachment 36. At the outer control portion 35, the arthroscope includes a portion of a lighting assembly 42, formed from a light source 41 that is connected to a light relay assembly 43. The lighting assembly 42 illuminates a viewing area beyond the object input end 32 of the housing tube 31. The viewing area is preferably an area in front of the object input end 32 of the arthroscope, from about 15 degrees below the longitudinal axis of the arthroscope tube 31 to about 105 degrees above the longitudinal axis of the arthroscope tube 31.

Figure 3:
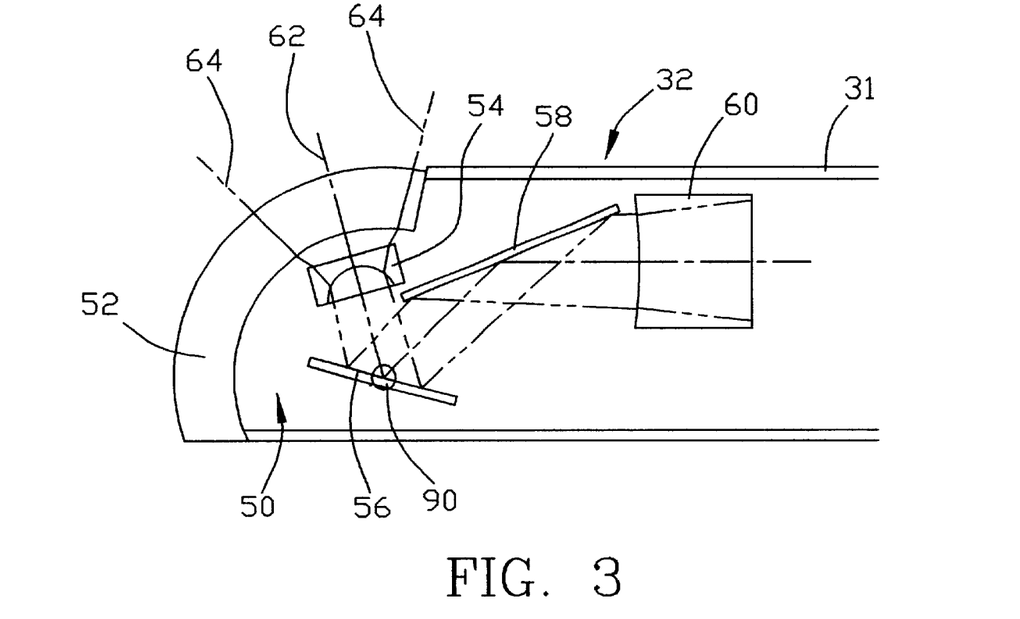
FIG. 3 is a sectional elevation view of the object input end of the arthroscope of FIG. 1, showing portions of an object input assembly in accordance with an embodiment of the present invention, adjusted for a maximum upward view.
Figure 4:
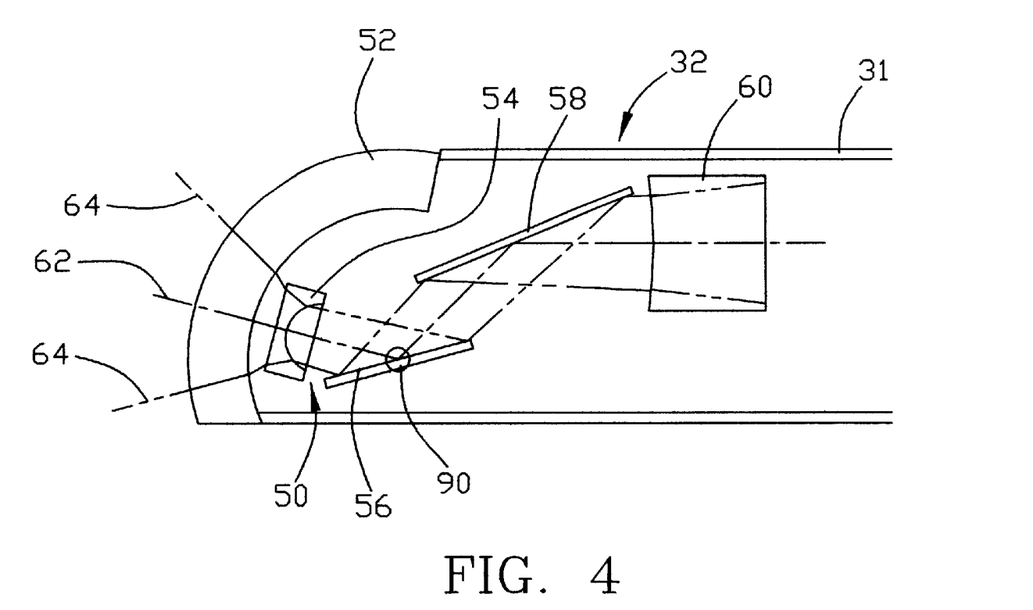
FIG. 4 is a sectional elevation view of the object input end of the arthroscope of FIG. 1, showing portions of an object input assembly, adjusted for a maximum downward view.
Figure 5:
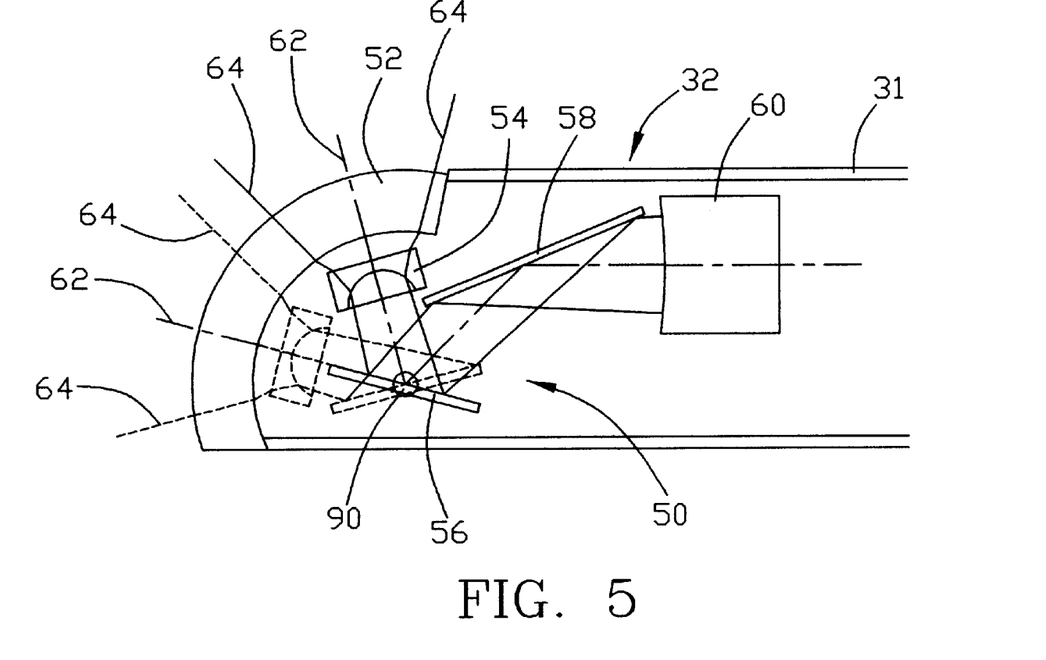
FIG. 5 is a sectional elevation view of the object input end of the arthroscope of FIG. 1, showing superimposed the portions of an object input assembly for the arthroscope adjusted for both a maximum upward view and a maximum downward view.
Figure 6:
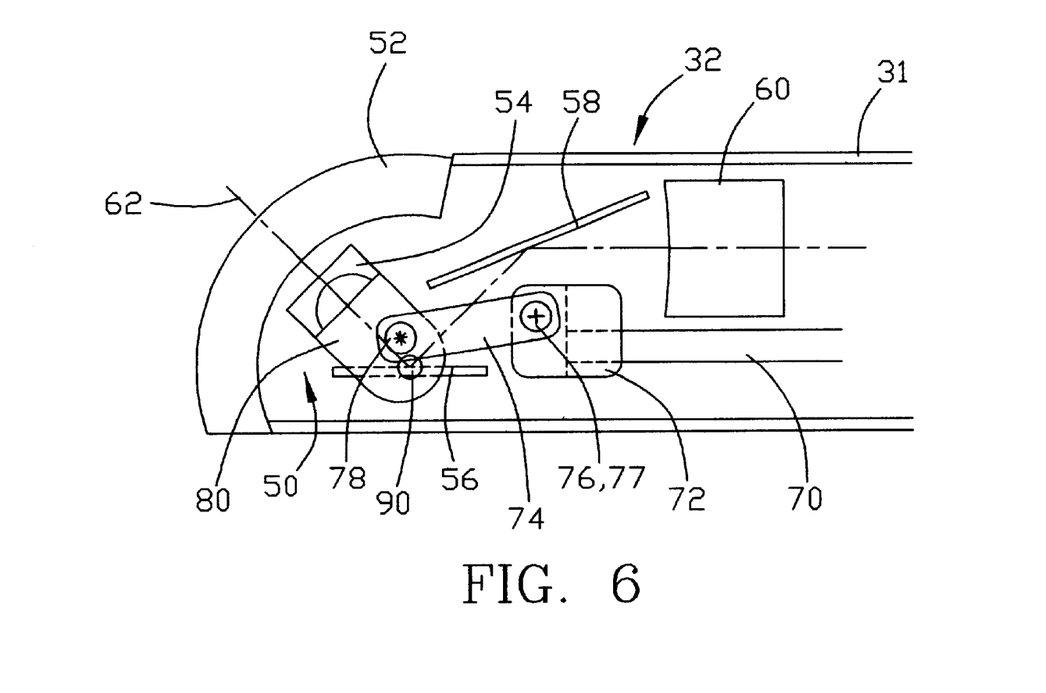
FIG. 6 is a sectional elevation view of the object input end of the arthroscope of FIG. 1, adjusted for an intermediate view, further showing an input lens control in accordance with an embodiment of the present invention.
Figure 7:
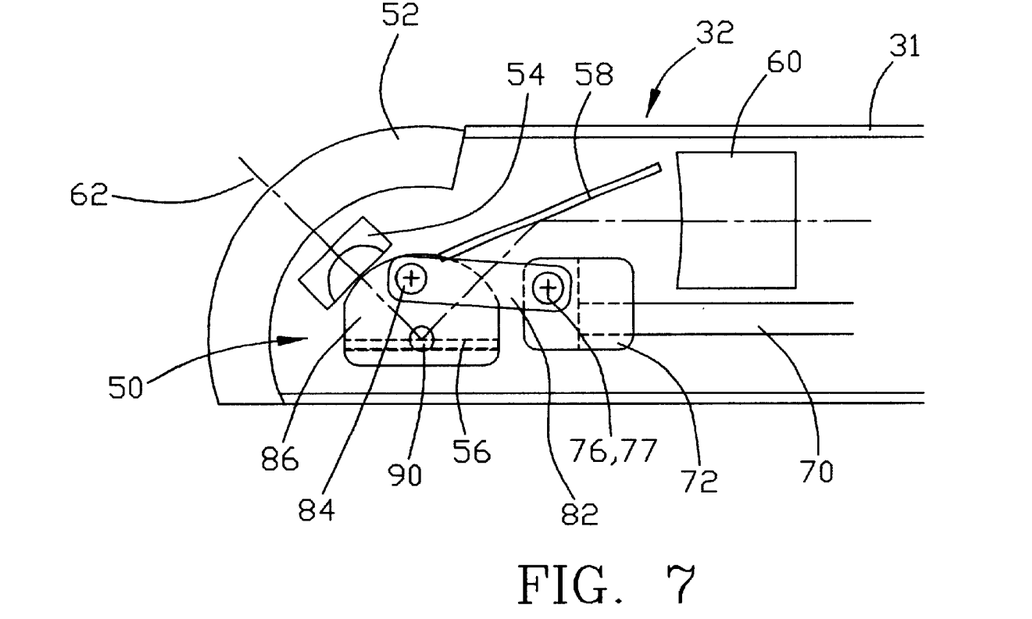
FIG. 7 is a sectional elevation view of the object input end of the arthroscope of FIG. 1, adjusted for an intermediate view, further showing a first mirror control, in accordance an embodiment of the present invention.
Figure 8:
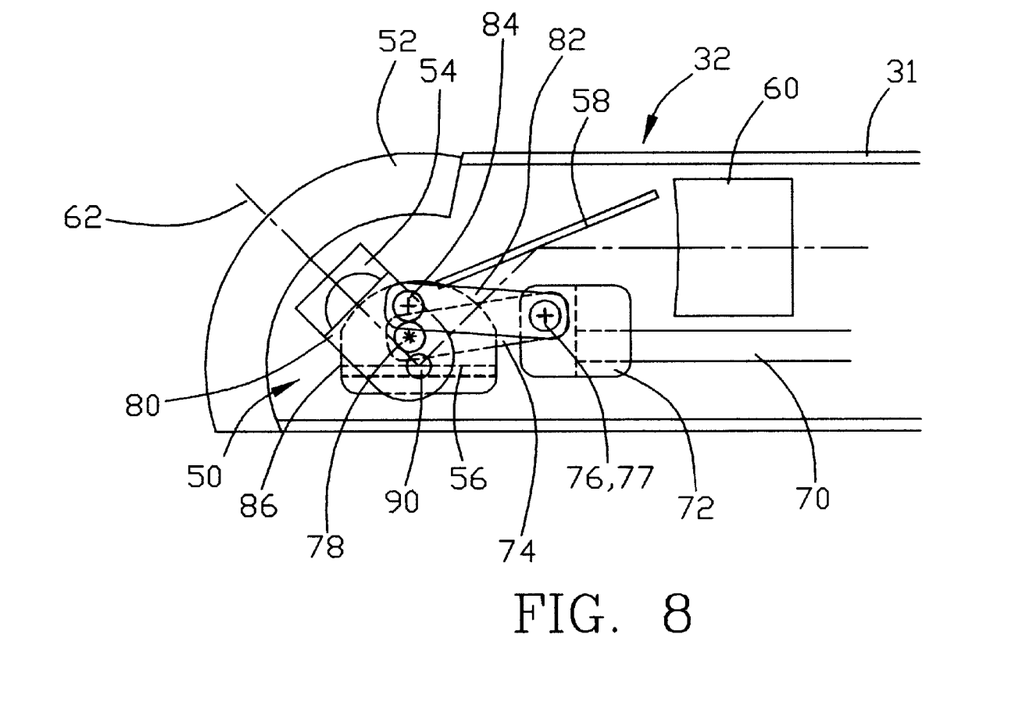
FIG. 8 is a sectional elevation view of the object input end of the arthroscope of FIG. 1, adjusted for an intermnediate view, showing both an input lens control and a first mirror control, in accordance with an embodiment of the present invention.
Figure 9:
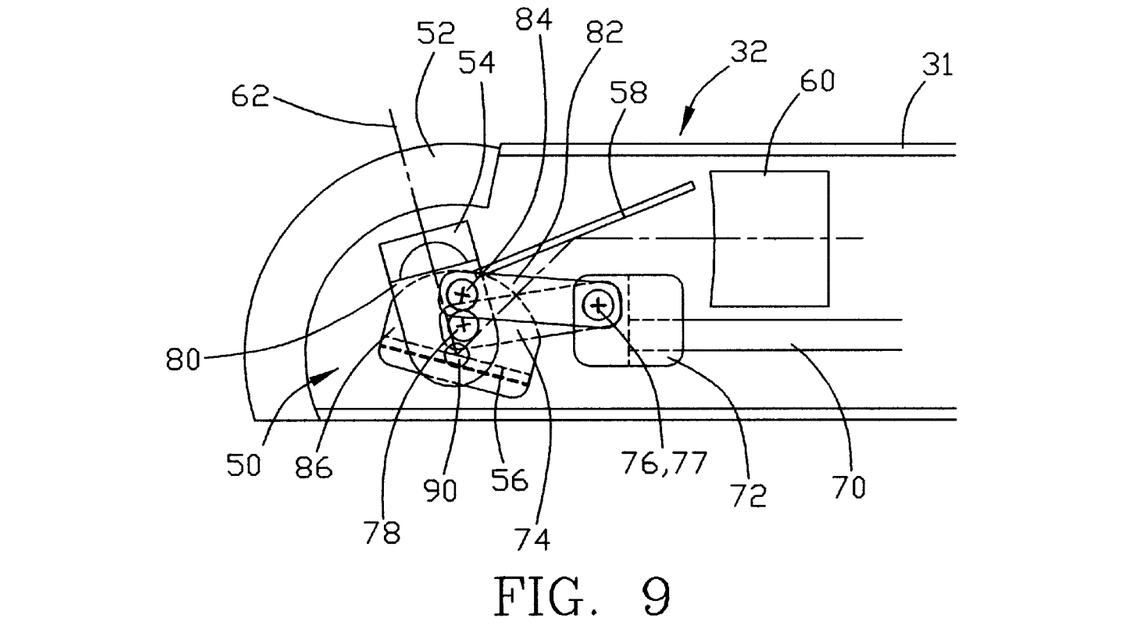
FIG. 9 is a sectional elevation view of the object input end of the arthroscope of FIG. 1, adjusted for a maximum upward view, showing both an input lens control and a first mirror control, in accordance with an embodiment of the present invention.
Figure 10:
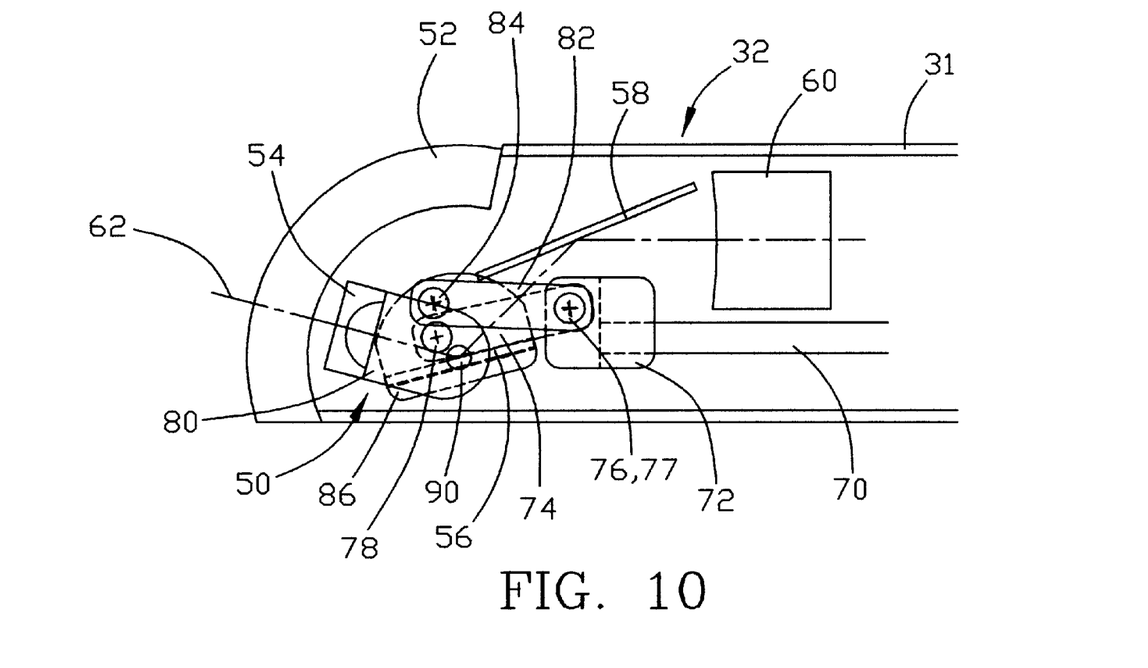
FIG. 10 is a sectional elevation view of the object input end of the arthroscope of FIG. 1, adjusted for a maximum downward view, showing both an input lens control and a first mirror control, in accordance with an embodiment of the present invention.

Referring now to FIGS. 3–5, the object input end 32 includes an object input assembly 50. In preferred embodiments, the object input assembly 50 includes an input window 52, an input lens 54, a first mirror 56 and a second mirror 58. In obtaining an image of the object, the object rays pass from the viewing area into the input window 52 and through the input lens 54, and are reflected from the first mirror 56 to the second mirror 58.

The input end 32 of housing tube 31 is preferably beveled and closed by input window 52. The input window 52 is preferably a concentric spherical meniscus lens and formed so that the curvatures of the outer and inner surfaces are concentric to each other around a common centerpoint. Preferably, the centerpoint is on the centerline of the axle 90, which is on the front reflecting surface of the first mirror 56 (as discussed further below). Also, preferably, the centerpoint is on the optical axis of the input lens 54. If the centerpoint of the input window 52 is positioned on the input lens optical axis, a constant relationship is maintained between the refractive angles of the input object rays as the input lens 54 moves from position to position. As a result, the refraction of the input object rays through the input window 52 is constant with respect to the input lens 54 and distortions are reduced. The dimensions of the input window 52 preferably are selected to maximize the range of view of the arthroscope 30 in cooperation with the other elements of the object input assembly. Input window 52 may be formed of glass or some other suitable material. The input window 52 is fixed in place, such as by adhesive, and also may be sealed to form a sealed closure for the end of the housing tube 31. Preferably, input end 32 of housing tube 31 is formed so that the edges of the housing tube 31 have a shape similar to the profile shape of the input window 52 and extend beyond the surface of input window 52 to afford the greatest protection to the input window 52 without interfering with the input object rays during operation of the arthroscope 30.

The input lens 54 and the first mirror 56 are movable and together vary the view of the arthroscope 30 and direct the captured image to the second mirror 58. The common axle around which both the input lens 54 and the first mirror 56 move and, with respect to which they are positioned, defines a preferred alignment of the input lens 54 and the first mirror 56. The input lens 54 of the object input assembly 50 is positioned inside the input end 32 of housing tube 31 proximate to the input window 52. In the embodiments illustrated in FIGS. 3–10, input lens 54 is a conic negative lens. However, any suitable lens may be used. The input lens 54 is movable and rotates around the axle 90. The input lens 54 rotates between a maximum upward view position (FIG. 3) and a maximum downward view position (FIG. 4), approximately corresponding to and limited by the field of view afforded by the input window 52. The input lens 54 is preferably fixedly mounted on an input lens frame 80. The input lens frame 80 supports the input lens 54 at one end and pivots around the axle 90 at the other end. The input lens frame 80 is moved by a control mechanism. The input lens 54 is mounted on the input lens frame 80 so that the optical centerline or axis of the input lens 54 is directed to the centerline of the axle 90.

The first mirror 56 is accordingly positioned to reflect the object rays received from the input lens 54 to the second mirror 58, which is fixed. The first mirror 56 pivots around the axle 90, in a motion complementary to that of the input lens 54. The centerline of the axle 90 is coplanar with the front reflecting surface of the first mirror 56. As the input lens 54 moves, the position of the first mirror must change to preserve the desired orientation of the object rays. Due to the geometry of mirrors, the angle change in a ray reflected from a mirror will be double rid the angle change in the reflecting plane of the mirror, such as when the mirror rotates from a first position to a second position.

Consequently, the first mirror 56 rotates around the axle 90 at half the rate of angular change at which the input lens 54 rotates around the axle 90, in a complementary direction. That is, as the input lens rotates around the axle 90 through a first angle of rotation, the first mirror 56 pivots around the axle 90 through a second angle of rotation that is half the first angle of rotation. The first mirror 56 correspondingly rotates between a maximum upward view position (FIG. 3) and a maximum downward view position (FIG. 4). Together with the movement of the input lens 54, the rotation of the first mirror 56 varies the view of the arthroscope 30. In alternative embodiments, the input lens 54 and the first mirror 56 may be moved between a series of pre-defined positions or may be moved to any position within the range of the arthroscope 30. The first mirror 56 is preferably mounted on a first mirror frame 86. A control adjusts the position of the first mirror 56. In the middle view of the object input assembly 50, the reflecting surface of the first mirror 56 is horizontal with respect to the longitudinal orientation of tube 3 land the input lens 54 is positioned so the optical axis of lens 54 is at an angle 45 degrees up from the plane of mirror 56. In the illustrated embodiment, the center of the middle view is therefore 45 degrees up from the horizontal (FIG. 6), i.e., the longitudinal axis of the tube 31.

The object rays obtained through the input lens 54, first mirror 56, and second mirror 58 are preferably relayed to the outer control portion 35 of the arthroscope 30 via the relay lens assembly 60. It is preferred that the rays be relayed so as to preserve the quality of the image and to minimize aberrations. The second mirror 58 is fixed in position to reflect the captured object rays into the relay lens assembly 60. The second mirror 58 is preferably aligned to orient the reflected object rays parallel to the optical axis of the relay lens assembly 60, which axis is preferably parallel to the longitudinal axis of the housing tube 31. The relay lens assembly 60 is preferably coaxial with the axial ray reflected from the second mirror 58. In various embodiments, the relay lens assembly 60 is a lens or a series of lenses, one alternative of which is commonly referred to as a field and relay lens system. In additional embodiments, the relay lens assembly 60 may be a graded index lens or other lens having a varying refractive index. In alternative embodiments, the relay lens assembly 60 may be replaced by an optical fiber coherent bundle. Although the relay lens assembly 60 is shown as being contained within the input end 32 of the housing tube 31, the relay lens assembly 60 typically extends further towards the control end 33. If the relay lens assembly 60 is replaced with a coherent bundle of optical fibers or is replaced with a graded index lens system, each will typically extend substantially along the length of housing tube 31. The relay lens assembly 60 may be of conventional construction, e.g., having an outer stainless steel sleeve for stability, or the relay lens assembly 60 may rest in a groove cut into relay light guide 120. The relay lens assembly 60 directs the object rays toward a receptor, such as a focusing lens assembly 55.

The movement of the input lens 54 and the first mirror 56 allows the viewing position of the arthroscope 30 and thus the particular input image captured in the arthroscope 30 to be variable. The control that adjusts the input lens 54 and the first mirror 56 adjusts them congruently to maintain the desired alignment. Referring to FIGS. 6–10, preferably, a push rod 70 directs the motion of the input lens 54 and the first mirror 56. The position of the input lens 54 is adjusted by the push rod 70 engaging the input lens frame 80 through an input lens connecting rod 74. The input lens connecting rod 74 is connected to the push rod 70 at push rod yoke 72 by yoke pin 76. The input lens connecting rod 74 is connected to the input lens frame 80 through an input lens frame pin 78. As the push rod 70 moves back and forth along the longitudinal axis of the housing tube 31, the connecting rod 74 shifts the position of the input lens frame 80 and, hence, of the input lens 54. The position of the first mirror 56 is adjusted by the push rod 70 engaging the first mirror frame 86 through a first mirror connecting rod 82. The first mirror connecting rod 82 is connected to the push rod 70 at push rod yoke 72 by yoke pin 77. Yoke pins 76 and 77 are disposed on opposite sides of the push rod yoke 72 and are coaxial. The first mirror connecting rod 82 is connected to the first mirror frame 86 through a first mirror frame pin 84. As the push rod 70 moves back and forth, the first mirror connecting rod 82 adjusts the angle of the first mirror 56.

The first mirror connecting rod 82 is fastened to the push rod yoke 72 at yoke pin 77 and the input lens connecting rod 74 is connected to the yoke at yoke pin 76. Because yoke pins 77 and 76 are coaxial, both connecting rods move synchronously. Preferably, the distance from the axle 90 to the input lens frame pin 78 is one half the distance from the axle 90 to the first mirror frame pin 84. As the push rod 70 moves laterally a certain distance, the angular change of the input lens 54 is preferably twice the angular change of the first mirror 56 since the radius of the input lens arc is one half the radius of the first mirror arc. The illustrated positioning and relative proportions of the connecting rods, axle and input lens frame pin and first mirror frame pin in FIGS. 8–10 preferably minimize any error in the relative angular changes. It should be understood that any mechanical arrangement that preserves the desired geometries of the mirrors and the input lens is suitable; for example, more than one push rod may be effective.

To minimize distortion in the recorded image, preferably, the object ray path lengths remain constant as the view of the arthroscope varies. The object axial ray 62 passes through the optical center of the input lens 54 to the center of the first mirror 56. This distance is fixed because the center of the first mirror 56 is fixed on the centerline of the axle 90 around which the input lens 54 rotates with a constant radius. The object axial ray 62 then reflects from the center of the first mirror 56 to the second mirror 58, which is fixed with respect to the first mirror 56. The axial ray then reflects from the second mirror 58 along the optical axis of the relay lens assembly 60, which is fixed with respect to second mirror 58. Because each segment of the object axial ray 62 has a fixed length, the length of the object axial ray 62 from the input lens 54 to the relay lens system 60 remains constant as the view of the arthroscope 30 varies. The object rim rays 64 pass through the input lens 54 to the first mirror 56. Because axial ray 62 is coaxial with the optical axis of input lens 52, all object rim rays 64 are symmetric about axial ray 62. As long as all object rays are reflected or refracted symmetrically to any plane normal to axial ray 62, such as the first lens of the relay lens system 60, the length of the object rays remain constant. In some embodiments of the present invention, this feature may allow the view to change without changes in distortion and image quality.

Figure 11:
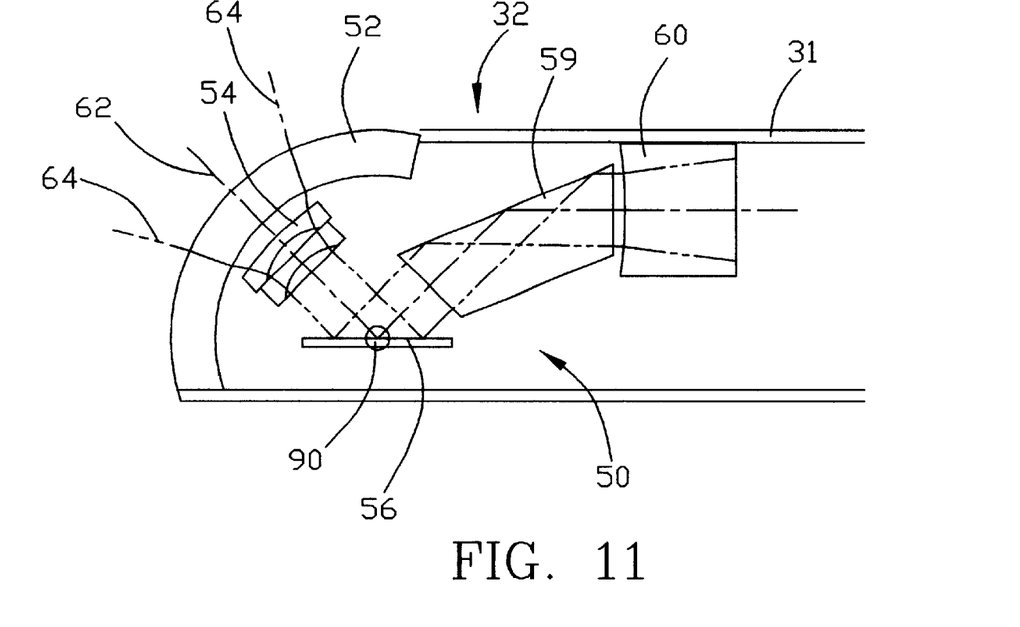
FIG. 11 is a sectional elevation view of the object input end of the arthroscope of FIG. 1, showing portions of an object input assembly, in accordance with another embodiment of the present invention, adjusted for an intermediate view.
Figure 12:
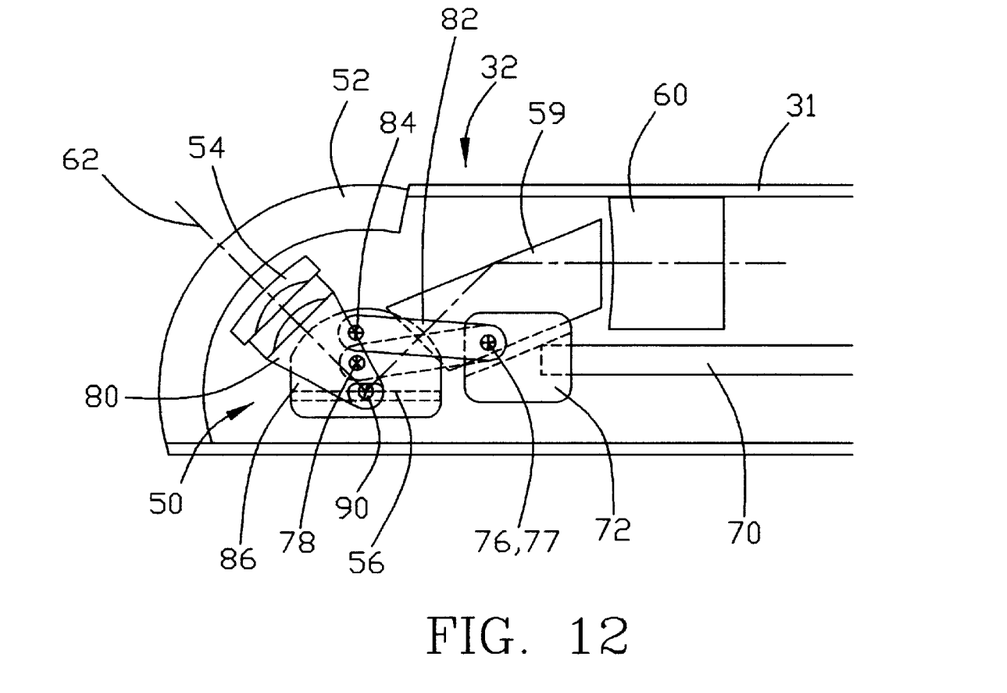
FIG. 12 is a sectional elevation view of the object input end of the arthroscope of FIG. 1, showing the portions of an object input assembly and related controls, in accordance with an embodiment of the present invention, adjusted for an intermediate view.

Referring now to FIGS. 11 and 12, in an alternative embodiment, rather than second mirror 58, a fixed prism 59 may orient the image rays reflected from the first mirror 56 into the relay lens assembly 60. The prism 59 receives object rays and internally reflects them in the desired direction. Because the input and output surfaces of prism 59 are normal to the object axial ray 62, and the object rim rays 64 are almost parallel at this point, the prism 59 preserves relative ray lengths similar to second mirror 58. Replacing second mirror 58 with prism 59 reduces the input lens system focal length, thereby improving image quality. Also, as illustrated in FIGS. 11 and 12, the input lens 54 may be a doublet consisting of two spherical lenses, which may be easier to construct than a single conic negative lens of very small size.

Figure 13:
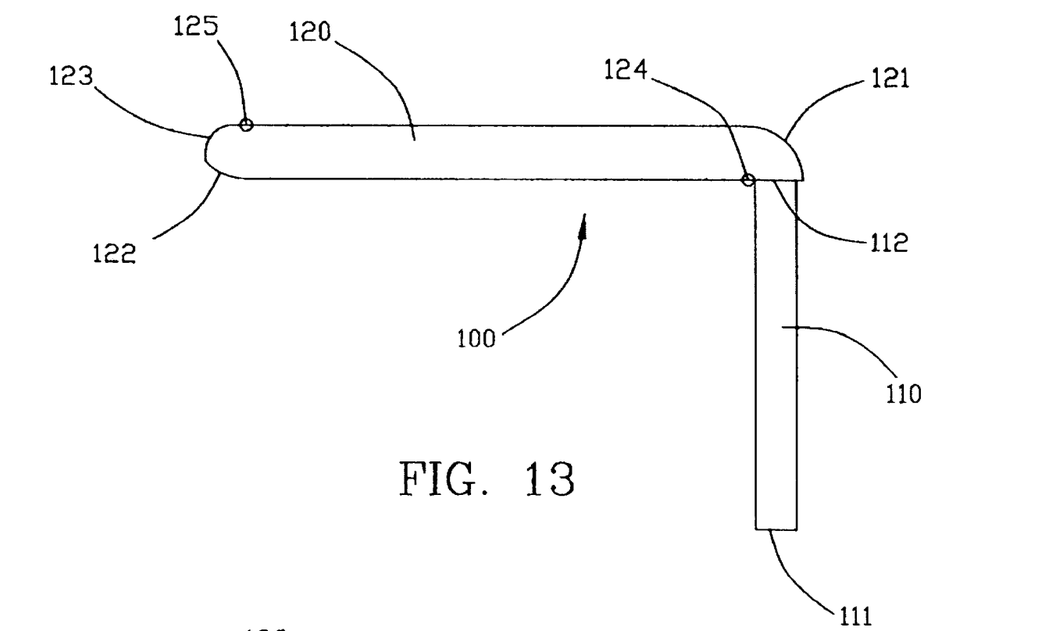
FIG. 13 is a sectional elevation view of a lighting system for an arthroscope in accordance with an embodiment of the present invention.
Figure 14:
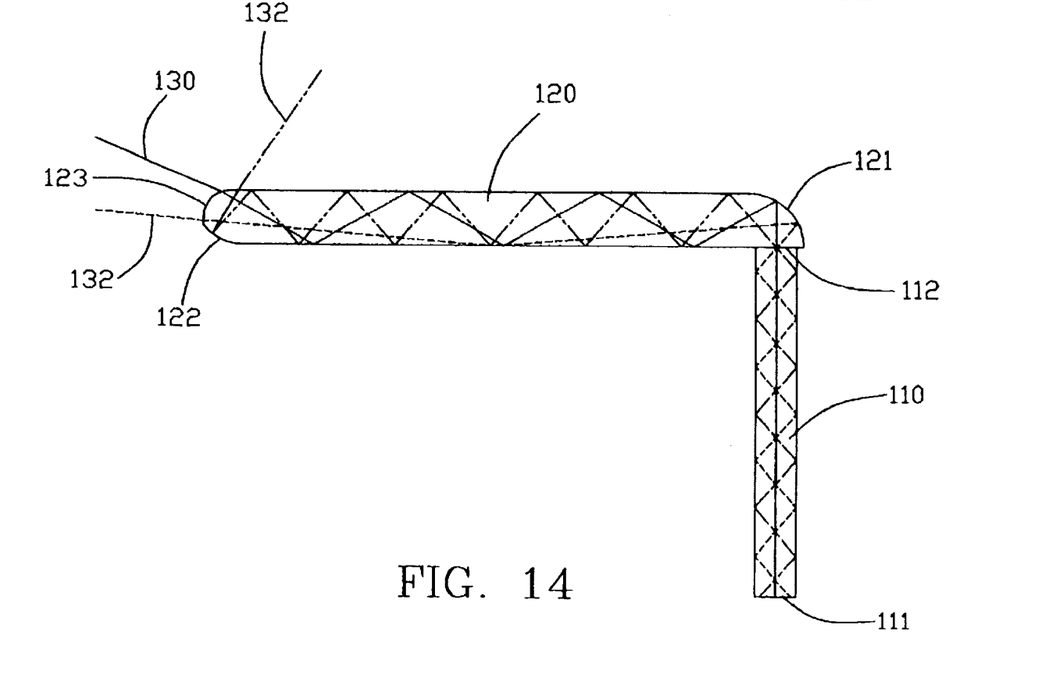
FIG. 14 is a sectional elevation view of the lighting system of FIG. 13, further showing the transmission of light rays through the system.
Figure 15A:
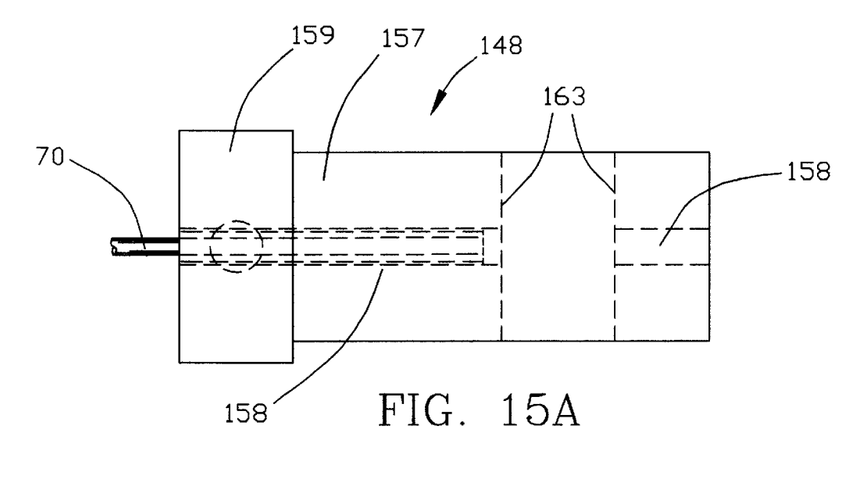
FIG. 15A is an elevation view of a slide portion of an arthroscope control in accordance with an embodiment of the present invention.
Figure 15B:
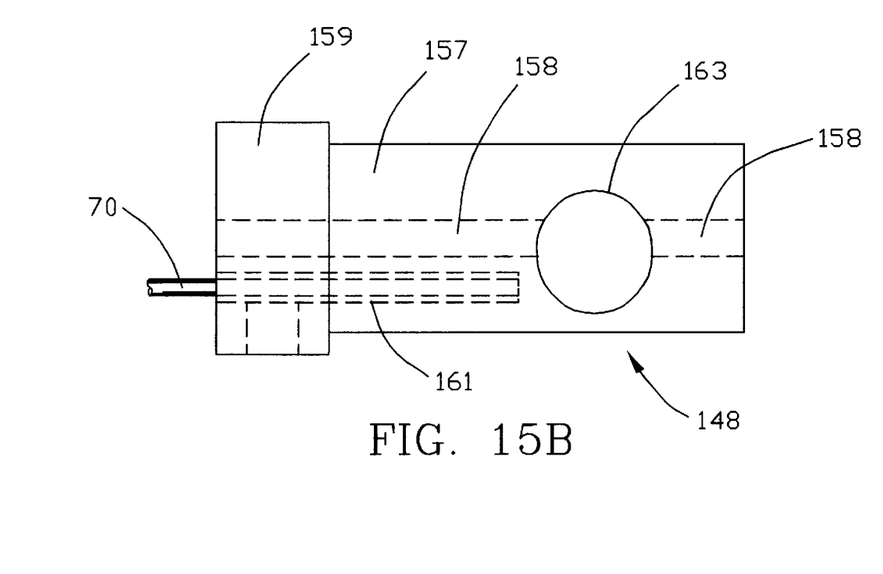
FIG. 15B is a plan view of the slide of FIG. 15A.
Figure 15C:
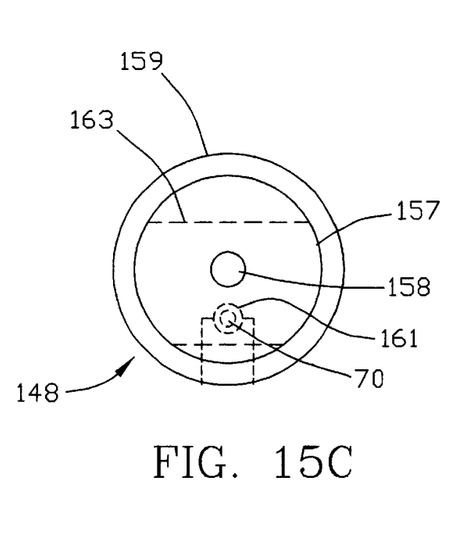
FIG. 15C is an end view of the slide of FIG. 15A.
Figure 16A:
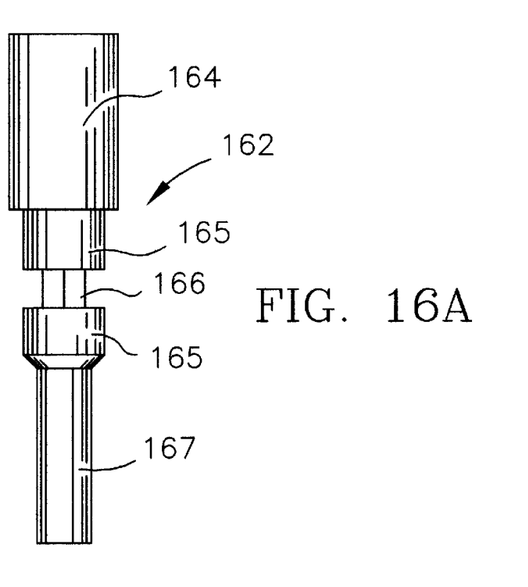
FIG. 16A is a plan view of a can/axle member of an arthroscope control in accordance with an embodiment of the present invention.
Figure 16B:
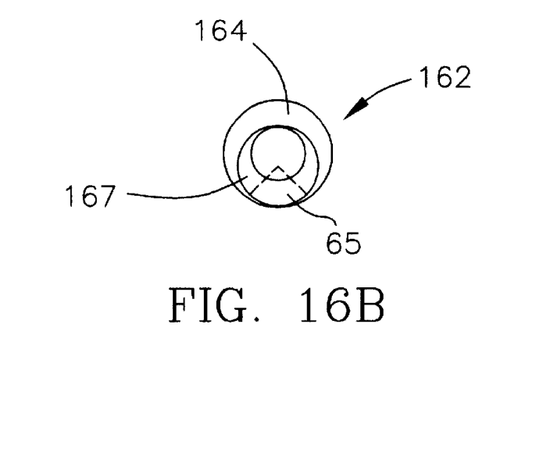
FIG. 16B is an end view of the cam/axle member of FIG. 16A.
Figure 16C:
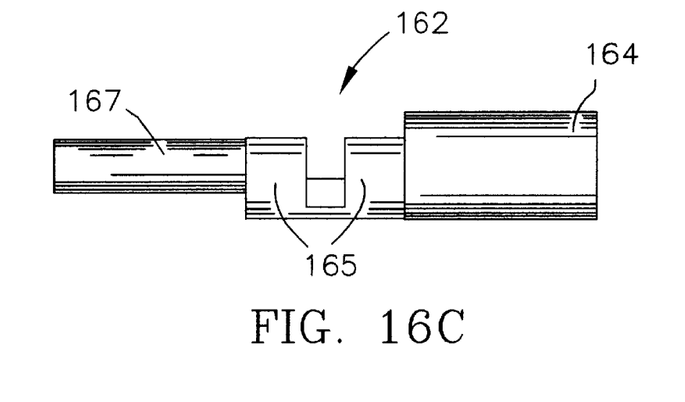
FIG. 16C is an elevation view of the cam/axle member of FIG. 16A.

The lighting assembly 42, illustrated in FIG. 2, includes a light source 41 with an external optical fiber light guide to transmit light to the light relay assembly 43 that extends into the arthroscope 30. Any conventional external light source and light guide may be used. Typically, the external light source 41 is connected at an angle oblique to the axis of the housing tube 31. The lighting assembly 42 may include a condenser lens to focus light from the external source 41 onto the input end of the light relay assembly 43. The light relay assembly 43 reorients the light along the longitudinal axis of the housing tube 31 and transmits the light to the end 32 of the housing tube 31. The light relay assembly 43 may include one or more optical fiber bundles. In some embodiments, the light relay assembly 43 is an optical fiber bundle that extends to the input end 32 of the arthroscope 30. In alternative embodiments, the light relay assembly 43 may include structures other than optical fiber bundles. Referring to FIGS. 13 and 14, in same embodiments, the light relay assembly 43 is a rod-based light relay assembly 100, including an input rod 110 and a relay rod 120. One advantage of some embodiments of rod-based light relay assembly 100 is that the cross-section is defined by only one rod and light is not lost as between the cores of fibers in a fiber optic bundle. The rods 110 and 120 are preferably joined to each other so that the input light guide rod 110 receives the light from the optical fiber light guide of the external light source 41 and transmits it to the relay rod 120. The relay rod 120 transmits the light from the input rod 110 to the distal end 32 of the arthroscope 30 to light the viewing area. The light relay assembly 100 is preferably designed to transmit the maximum amount of light from the light source to the viewing area. The light relay assembly 100 preferably is designed to accommodate light that is skewed with respect to the optical axis of the light relay assembly; the light may typically be skewed by 40 degrees or more from the optical axis. Each of the optical fibers of the external light guide of the external light source 41 emits a cone of light equal to twice the numerical aperture of the fiber. At the edge of each cone are the maximum skew rays and at the center of each cone is the central ray. In between the maximum skew rays, an infinite number of rays fans out from the central ray. Preferably every ray is transmitted to the viewing area. FIG. 14 illustrates the path of both a central ray 130 and skew rays 132 that are transferred through the light relay assembly 110.

The input rod 110 and the relay rod 120 are formed from plastic or other transparent material, such as acrylic or polycarbonate, that is suitable to act as a light guide. The relay rod is preferably positioned so that it extends at an angle to the input rod, for example so that it is perpendicular, to accommodate the orientation of the external light source 41 with respect to the housing tube 31 and redirect the light along the axis of the tube 31. Light from the external source 41 enters the input rod 110, turns where the input rod 110 joins the relay rod 120, and passes out the opposite end of the relay rod 120 through the input window 52 to the viewing area. Both the input rod 110 and the relay rod 120 have entirely mirrored surfaces except for the input end and the output end of each. Because of the mirrored surfaces, light relay assembly 100 does not depend on the numerical aperture limits of total internal reflection to gather and transmit light through its length. As a result, mismatched spot sizes, optical fiber core locations, and mismatched numerical apertures do not cause loss of light-gathering and transmission efficiency as often occurs in optical fibers. Preferably, every ray entering the input rod 110 is reflected into the relay rod 120 at the joint between the input rod 110 and the relay rod 120 and through the relay rod 120 to the viewing area.

The input rod 110 is mirrored on its surface except at its input face 111 and output face 112. Preferably, the diameter of the input rod 110 is equal to or slightly larger than the overall diameter of the external light guide. Preferably, the diameter of the relay rod 120 is larger then the diameter of the input rod 110. With the rods 110, 120 positioned at a 90 degree or other angle from one another, a larger difference in the diameter of the rods 110, 120 will improve the efficiency of the turning of the light. The diameter of relay rod 120 is determined by the available space inside tube 31. The curve 121 is preferably dimensioned to ensure that the maximum skew ray is reflected down the length of relay rod 120 and not back through input rod 110. The angle of the maximum skew ray depends on the light that is emitted from the external source 41. The input end of the relay rod 120 is curved at the surface 121 where light entering from the input rod reflects, i.e., the surface 121 opposite the surface where the relay rod 120 is joined to the input rod. Preferably, the radius of the curve 121 is substantially equal to or larger than the diameter of the relay rod 120. Preferably, referring to the illustrations in FIGS. 13, the center 124 of the curve 121 is to the left of the left edge of the input rod 110.

The relay rod 120 preferably extends along the longitudinal axis of the housing tube 31 and ends near the input window 52 of the arthroscope 30. The relay rod 120 is mirrored on its surface except where it receives light from the input rod 110 on face 112 and where it releases light at surface 123. The output end of the relay rod 120, proximate to the input window 52, has an upper curved portion 123 and a lower curved portion 122. The lower curved portion 122 is mirrored to reflect light in the desired direction, i.e., out the input window 52. The upper curved portion 123 is clear to allow the transmitted light to escape through the end of the rod 120 through the window 52 to illuminate the viewing area. Preferably, together the lower curved portion 122 that is mirrored and the upper curved portion 123 that is clear provide as much light as possible to the viewing area and reduce diffusion of light into non-working areas that need not be illuminated. The location of the center of the lower curved surface 122 and length of the lower curved surface 122 determine the angle from which the viewing area will be lighted and the amount of light directed to the working area. The radius of the lower mirrored curved surface 122 is preferably equal to or larger than the diameter of the relay rod 120. Referring to the illustration in FIGS. 13, the center 125 of the lower curve 122 is to the left of the end of the mirrored surface on the upper portion of the relay rod end. Preferably, every light ray will be reflected forward toward the viewing area by surface 122 and not back through the relay rod 120. The proportions of the upper curved surface 123 also determine the amount of light and direction of the light rays leaving the relay rod 120. The upper curved surface 123 is preferably designed so that light rays reflecting from the lower curved surface 122 strike the upper curved surface 123 at less than the critical angle of upper curved surface 123, and escape rod 120, rather than internally reflecting back through the rod 120. The upper curved surface 123 preferably diffuses the light with an even distribution across the viewing area. The exact proportions of the upper and lower surfaces 122, 123 will depend on the desired illumination properties of the arthroscope 30 for the viewing area.

FIGS. 15A–18D illustrate a mechanism for manipulating the push rod to operate the object input assembly control and adjust the view of the arthroscope 30. At the control end 35 of the arthroscope 30 the push rod 70 extends into and engages a slide 148. The slide includes a main body 157 having an axial relay lens opening 158; the relay lens opening 158 also extends through an enlarged end 159 of the slide 148. A socket 161 aligns and attaches push rod 70 to slide 148. In the illustrated embodiment, the control rod socket 161 is located directly below the axial opening 158 for the relay lens.

Figure 17A:
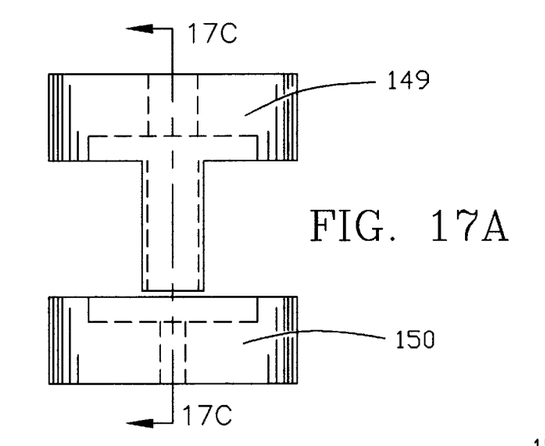
FIG. 17A is a plan view of two control knobs of an arthroscope control in accordance with an embodiment of the present invention.
Figure 17B:
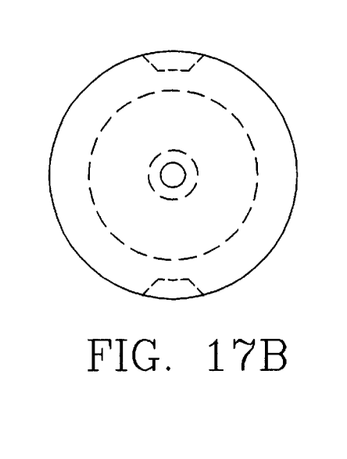
FIG. 17B is an end view of the control knobs of FIG. 17A.
Figure 17C:
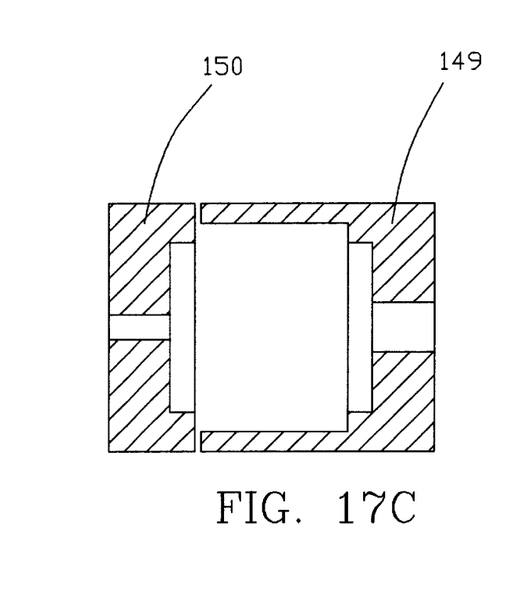
FIG. 17C is a sectional view, along line 17c—17c in FIG. 17A, of the control knobs.
Figure 18A:
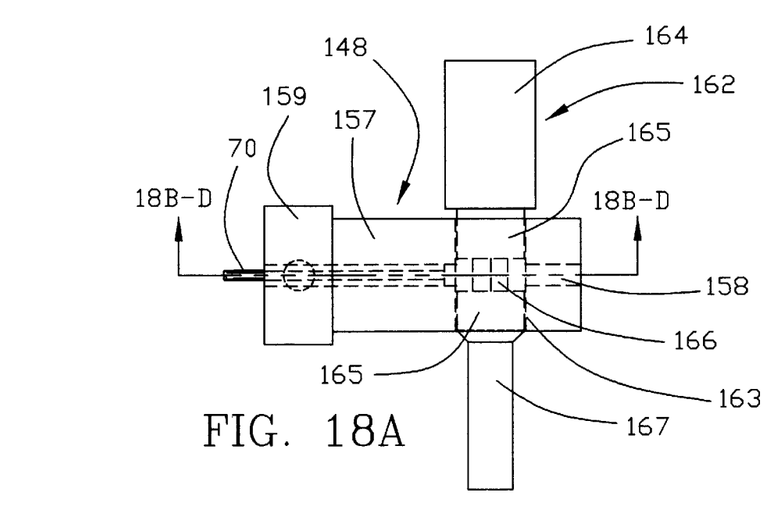
FIG. 18A is a plan view of the slide and cam/axle relationship in the center travel position in accordance with an embodiment of the present invention.
Figure 18B:
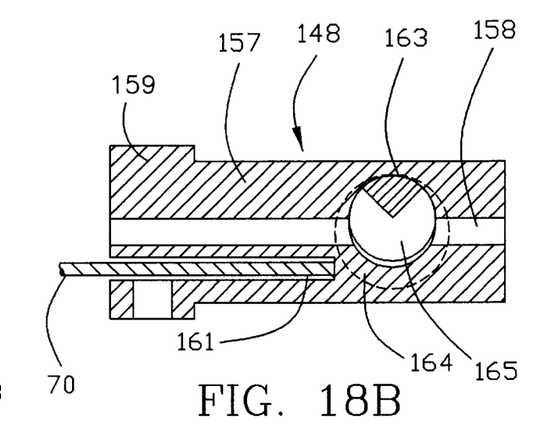
FIG. 18B is a sectional view along line 18B-D in FIG. 18A showing the slide and cam/axle relationship in the center travel position in accordance with an embodiment of the present invention.
Figure 18C:
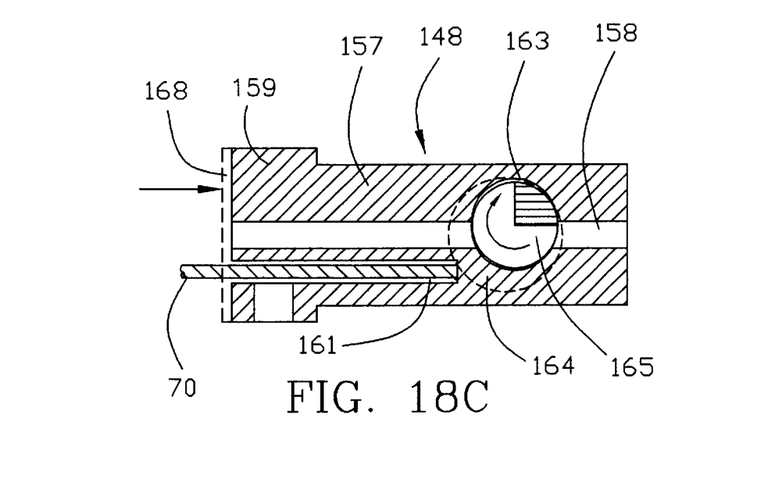
FIG. 18C is a sectional view along line 18B-D in FIG. 18A showing the slide and cam/axle relationship in the full aft travel position in accordance with an embodiment of the present invention.
Figure 18D:
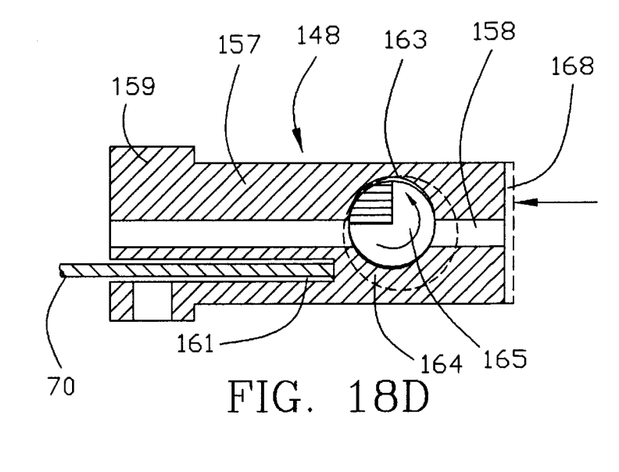
FIG. 18D is a sectional view along line 18B-D in FIG. 18A showing the slide and cam/axle relationship in the full forward travel position in accordance with an embodiment of the present invention.

The cam portion 165 of cam/axle member 162 is positioned in a central transverse opening 163 in slide 148. Opening 163 is not quite circular in cross-section; it is enlarged or stretched slightly. The cam/axle member 162 includes a large control knob shaft attachment segment 164 of circular cross-section; a circular off-axis cam segment 165 contains a relay lens assembly slot 166, and a small control knob shaft attachment segment 167. Two control knobs, 149, 150 shown in FIGS. 17A–17C, are mounted on the outer ends 164 and 167 of cam/axle member 162. The control knobs 149, 150 include a righthand control knob 149 that is fitted onto the large control wheel shaft attachment segment 164 of the cam/axle member 162. The second or lefthand control knob 150 fits onto the smaller control knob shaft attachment segment 167 of cam/axle member 162. Rotation of the control knobs 149, 150 that are attached to cam/axle 162 cause the off-axis cam 165 of cam/axle 162 to engage the central transverse opening 163 of slide 148, causing slide 148 to move laterally, as indicated by dashed areas 168 in FIGS. 18C and 18D, in response to the rotary motion of cam/axle 162.

In alternative embodiments, the slide 148 may also be electrically driven. Slide 148 may be driven by a step motor. A step motor may drive cam/axle 162, or cam/axle 162 may be replaced with, for example, a jack screw engaging slide 148. The step motor and jack screw are preferably internal to the arthroscope 30 and mounted parallel to the motion of slide 148. Slide 148 may also be driven with a piezoelectric positioner mounted internally to the arthroscope 30. The arthroscope 30 may be electrically operable by electrical buttons or by operating software on a computer, for example.

Operation of the arthroscope 30 can now be considered. At the outset, light from external source 41 is focused upon the end of the light relay assembly 43, which is preferably a rodbased light relay assembly 100. Light passes through the light relay assembly 43 and illuminates a surgical working area just beyond the input end 32 of the arthroscope 30. In arthroscope 30, light passing through light relay assembly 43 may reflect, at least in part, from the second mirror 58 onto the reflective surface of the first mirror 56, and then pass through the input lens 54 into the viewing area to be illuminated. Light reflected from the viewing area passes through input window 50 and input lens 54 as object rays which impinge on first mirror 56. The object rays are directed from the first mirror 56 to impinge upon the second mirror 58 or prism 59. From the second mirror 58 or prism 59 the object rays are re-directed toward the input end of the relay lens assembly 60. The relay lens assembly 60 supplies the image to the CCD attachment 36, through focusing lens assembly 55, to be viewed by the surgeon or other person using the arthroscope 30.

If the person using arthroscope 30 is dissatisfied with the image available through the CCD attachment 36, control knobs 149, 150 may be used to provide an image of a different portion of the surgical region. In this way the image supplied to the surgeon or other person using the instrument 30 can be and is varied to a substantial extent with no change in the position of the instrument. In effect, the overall viewing range of the instrument 30 may extend from about 15 degrees below the longitudinal axis of the housing tube to about 105 degrees above the axis of the housing tube, with no need to change the axis of the instrument. Further alteration or correction of the image may be effected by appropriate software.

Several parts of instrument 30 can be modified from those illustrated without appreciable effect on overall operation of instrument 30. For example, the push rod 70 may be modified; the push rod 70 constitutes an optional mechanism for operating the input lens and first mirror but any mechanism that will move the input lens and first mirror in the relationship described can be used. The cam/axle and slide control mechanism may also be altered. The angle of the bevel of the outer end of housing tube 31 may be varied as desired; a curved shaped similar to the profile shape of the input window and extending beyond the input window so as to provide maximum protection to the input window without interfering with the object rays is preferred, but may depend on the primary use for instrument 30. It will be recognized that use of a CCD unit for a display is not essential. The software used for the display may vary appreciably.

The language used herein is used for purposes of reference and not limitation. While the invention has been particularly shown and described with reference to preferred embodiments, it will be apparent to those skilled in the art that various modifications and alterations can be made in the device of the present invention without departing from the spirit and scope of the invention.

What is claimed is:

1. A variable view arthroscope having more than one viewing position, including a first viewing position and a second viewing position, comprising:
   an input lens rotatable around a common axis;
   a first mirror rotatable around the common axis, the common axis being coplanar with a reflecting surface of the mirror;
   an object relay assembly;
   wherein, the input lens, the first mirror and the object relay assembly are arranged so that object rays pass through the input lens to the first mirror and reflect from the first mirror toward the object relay assembly, and
   wherein the angular rotation of the first mirror around the common axis between the first viewing position and the second viewing position is half the angular rotation of the input lens around the common axis between the first viewing position and the second viewing position.

2. The variable view arthroscope of claim 1, further comprising a fixed aligning optical element, the fixed aligning optical element being positioned so that object rays reflect from the first mirror to the aligning optical element and from the aligning optical element into the object relay assembly.

3. The variable view arthroscope of claim 2, further comprising a housing tube enclosing the input lens, the first mirror, the aligning optical element and the object relay assembly, the housing tube having a viewing end, the viewing end being closed by an input window, the input window being spherical and having a first surface with a curvature and a second surface with a curvature, the curvatures of the first and second surfaces of the input window being concentric around a common centerpoint.

4. The variable view arthroscope of claim 2, wherein the aligning optical element is a second mirror.

5. The variable view arthroscope of claim 2, wherein the aligning optical element is a prism.

6. The variable view arthroscope of claim 2, wherein the input lens is a conic negative lens.

7. The variable view arthroscope of claim 2, wherein the input lens is a doublet of two spherical lenses.

8. The variable view arthroscope of claim 1, further comprising a housing tube enclosing the input lens, the first mirror, the aligning optical element and the object relay assembly, the housing tube having a viewing end, the viewing end being closed by an input window, the input window being spherical and having a first surface with a curvature and a second surface with a curvature, the curvatures of the first and second surfaces of the input window being concentric around a common centerpoint.

9. The variable view arthroscope of claim 8, wherein the common centerpoint is on the common axis.

10. The variable view arthroscope of claim 1, further comprising an input lens frame, wherein the input lens is mounted on a first end of the input lens frame, the input lens frame having a second end proximate to the common axis and having a pivot point at the common axis.

11. The variable view arthroscope of claim 10, further comprising a control, the control including a push rod having a slide end and an input assembly end.

12. The variable view arthroscope of claim 11, the control further including a push rod yoke attached to the push rod at the input assembly end, an input lens connecting rod attached to the push rod yoke by a first yoke pin and to the input lens frame by an input lens frame pin, the first mirror being mounted on a first mirror frame, and a first mirror connecting rod attached to the push rod yoke by a second yoke pin and to the first mirror frame by a first mirror frame pin, the first and second yoke pins being coaxial.

13. The variable view arthroscope of claim 12, wherein the distance from the common axis to the input lens frame pin is half the distance from the common axis to the first mirror frame pin.

14. The variable view arthroscope of claim 11, the control further including a slide attached to the push rod at the slide end, the slide being longitudinally movable, a cam-axle assembly for moving the slide, and a view control to manipulate the cam-axle assembly.

15. The variable view arthroscope of claim 1, wherein the optical axis of the object rays intersects the common axis in the first viewing position and in the second viewing position.

16. The variable view arthroscope of claim 1, further comprising a first mirror frame, wherein the first mirror is mounted on the first mirror frame, the first mirror frame having a pivot point at the common axis.

17. A variable view arthroscope, comprising:

an input lens which is rotatable;

a first mirror which is rotatable; and an object relay assembly; wherein the input lens, first mirror and object relay assembly are arranged to cooperate to capture and direct object rays so that the rays pass through the input lens to the first mirror, and reflect from the first mirror towards the object relay assembly, rotation of the input lens varying the view of the arthroscope, and wherein the angle of rotation of the first mirror is coordinated to be half the angle of rotation of the input lens.

18. The variable view arthroscope of claim 7, wherein the input lens and the first mirror are rotatable around a common axis and the common axis is coplanar with a reflecting surface of the first mirrors .

19. The optical system of claim 17, further comprising a second mirror, wherein the first mirror reflects object rays to the second mirror and the second mirror directs object rays to the object relay assembly.

20. The variable view arthroscope of claim 19, wherein the second mirror fixed.

21. The variable view arthroscope of claim 18, wherein the optical axis of the object rays intersects the common axis as the view of the arthroscope is varied.

22. The variable view arthroscope of claim 17, further comprising wherein the object relay assembly is a relay lens system, further comprising a prism, wherein the first mirror reflects object rays to the prism and the prism directs object rays into said relay lens system.

23. The variable view arthroscope of claim 22, the relay lens system having an optical center, wherein the prism is fixed and is oriented to reflect an axial object ray received from the first mirror to the optical center of the relay lens system.

24. The variable view arthroscope of claim 17, wherein the input lens and the first mirror are rotatable around a common axis and the common axis is transverse to the optical axis.

* * * * *